United States Patent [19]
Irie et al.

[11] Patent Number: 6,054,606
[45] Date of Patent: Apr. 25, 2000

[54] METHOD FOR PREPARING MALONATE GROUP-CONTAINING ACRYLATE MONOMERS

[75] Inventors: Takashi Irie, Suita; Kei Aoki, Ikoma, both of Japan

[73] Assignee: Nippon Paint Co., Ltd., Osaka, Japan

[21] Appl. No.: 08/861,015

[22] Filed: May 21, 1997

[30] Foreign Application Priority Data

May 22, 1996 [JP] Japan .................................. 8-151544

[51] Int. Cl.[7] ........................... C07C 69/34; C07C 69/52
[52] U.S. Cl. ............................................ 560/201; 560/199
[58] Field of Search ..................................... 560/201, 199

[56] References Cited

FOREIGN PATENT DOCUMENTS 0 413 290  2/1991  European Pat. Off. .

*Primary Examiner*—Paul J. Killos
*Attorney, Agent, or Firm*—Millen, White, Zelano, & Branigan, P.C.

[57] ABSTRACT

A malonate group-containing acrylate monomer is produced by a transesterification reaction of dialkyl malonate with a hydroxyalkyl (meth)acrylate or a polyalkylene glycol mono (meth)acrylate. The malonate group-containing acrylate monomer finds use in the production of an acrylic polymer capable of crosslinking through a Michael reaction with an α, β-unsaturated carbonyl compound or resin.

10 Claims, No Drawings

METHOD FOR PREPARING MALONATE GROUP-CONTAINING ACRYLATE MONOMERS

BACKGROUND OF THE INVENTION

This invention relates to a method for preparing malonate group-containing acrylate monomers.

Michael reactions in which base-catalyzed addition of activated methylene to polarized double bond are utilized in the crossling reaction of resinous compositions for coating use. These compositions are advantageous in that the Michael reaction gives a chemically stable crosslinking bond without forming any reaction by-product.

Typical examples of activated methylene compounds used in the Michael reaction are acetoacetates, cyanoacetates and malonates. For use in the crosslinking reaction of resins or polymers, the Michael donor must be a compound or polymer having a plurality of activated methylene groups in the molecule. Acrylic monomers having an acetoacetoxy group can be synthesized relatively easily by reacting diketene with a hydroxylalkyl acrylate or methacrylate such as 2-hydroxyethyl acrylate (HEA) or 2-hydroxylethyl methacrylate (HEMA). Activated methylene-containing acrylic polymers used in the prior art are either polymers of acetoacetylated hydroxyalkyl (meth)acrylate monomers or acetoacetylated acrylic polyols produced by reacting diketene with an acrylic polyol polymer.

Because malonic acid is a dibasic acid, malonate groups can be incorporated into a polyester chain to produce a polymeric Michael donor. U.S. Pat. No. 4,602,061 discloses a liquid two-component coating composition comprising (a) an oligomeric or polymeric malonate compound such as polyurethanes, polyesters, polyacrylates, epoxy resins, polyamids or polyvinyl resins containing malonate groups, either in the main chain or the side chain or in both, (b) an α, β-ethylenically unsaturated carbonyl compound and (c) a basic catalyst.

The malonate group-containing polyacrylate resin disclosed therein is a reaction products of the above-mentioned malonate polyester resin first with a diisocyanate and then with HEA or HEMA.

JP-A-03206012 discloses a series of acrylic monomers in which one of carboxyl groups of an aliphatic dicarboxylic acid such as malonic, succinic or glutaric acid is esterified with an alkanol while the other carboxylic acid is esterified with an alkanol. These monomers are used for the production of odorless, low irritating and low water absorption polymeric dental materials. Although 2-(methoxymalonyloxy)ethyl methacrylate otherwise called 2-methacryloyloxyethyl methyl malonate is named, its production method is not specifically disclosed. Instead, it is taught that the malonate monomer can be produced in the same manner as the corresponding succinate monomer which is produced by reacting succininc anhydride with HEMA and then reacting the resulting half ester with methanol. Because malonic anhydride does not occur, this method is not applicable to the malonate monomer.

It has been discovered that acrylic polymers having malonate group-containing pendant groups exhibit higher weatherability than the corresponding polymers having actoacetate-terminated pendant groups when used for coating purposes. This is because the terminal structure of activated methyle is a stable ester linkage.

A need exists, therefore, for a method for preparing a malonate group-containing acrylate monomer which is suited for large scale production of the malonate monomer efficiently starting from easily available materials.

SUMMARY OF THE INVENTION

The present invention provides a method for preparing a malonate group-containing acrylate monomer comprising heating a hydroxyl group-containing acrylic monomer of the formula I:

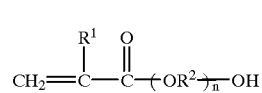

(I)

wherein $R^1$ is hydrogen or methyl, $R^2$ is a $C_2$–$C_6$-alkylene, and n is an integer from 1 to 10, and an excess of a dialkyl malonate in the presence of a catalyst and a polymerization inhibitor while bubbling with a gas; and removing an alcohol produced as a reaction by-product from the system during the heating step.

The present invention also provides a malonate group-containing acrylate monomer of the formula II:

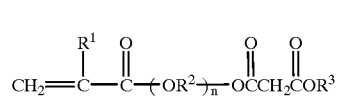

(II)

wherein $R^1$, $R^2$ and n are as defined, and $R^3$ is a $C_1$–$C_6$-alkyl with the proviso that when $R^1$ is methyl, $R^2$ is ethylene and n is 1, $R^3$ cannot mean methyl.

DETAILED DISCUSSION

One of starting materials of the formula I is hydroxyalkyl (meth)acrylate (n=1) or polyalkylene glycol mono(meth)acrylate (n>1). Examples of hydroxylalkyl (meth) acrylate include 2-hydroxyethyl acrylate (HEA), 2-hydroxyethyl methacrylate (HEMA), 2-hydroxylpropyl (meth) acrylate, 3-hydroxypropyl (meth)acrylate, 2-hydroxybutyl (meth) acrylate, 4-hydroxylbutyl (meth)acrylate, and 3-hydroxybutyl (meth)acrylate. HEA and HEMA are preferable. Polyalkylene glycol mono(meth)acrylates are derived from acrylic or methacrylic acid and a ring opening polymerization product of an alkylene oxide or cyclic ether such as ethylene oxide, propylene oxide or tetrahydrofuran. Polyethylene glycol mono(meth)acrylate, polypropylene glycol mono(meth)acrylate and polytetramethylene glycol mono(meth) acrylate are commercially available.

Dialkyl molanates are also commercially available as starting materials of, for example, barbiturate drugs. Examples thereof include dimethyl malonate, diethyl malonate, dipropyl malonate, dibutyl malonate, dipentyl malonate, dihexyl molanate, diheptyl malonate, diocytyl malonate, diisopropyl malonate, and di-t-butyl malonate. Asymmetric dialkyl malonates may also be used.

As is well-known, a transesterification reaction is accelerated in the presence of a catalyst such as a Bronsted acid/base, Lewis acid/base, or solid acid/base. Examples of catalysts include acids such as p-toluenesulfonic acid, dodecylbenzenesulfonic acid, sulfuric acid, hydrochloric acid, nitric acid, boric acid, phosphoric acid, pyrophosphoric acid, polyphosphoric acid, phosphonic acid, phosphinic aicd or a stongly acidic cation exchange resin; bases such as triethylamaine, 1,4-diazabicyclo[2.2.2] octane known as DABC, 1,8-diazabicyclo[5.4.0]undeane-7, pyridine, sodium methoxide, sodium ethoxide, potassium t-butoxide or hexamethylphosphoric triamide; organic tin compounds such as dibutyltin dilaurate or dibultin oxide; mixted catalysts such as dimethyltin iodide/tetraphenylantimony iodide or dimethyltin iodide/hexamethylphosphoric triamide; metal oxides such as antimony trioxide or lead dioxide; metal acetates such as manganese acetate, cobalt acetate, calcium acetate, lithium acetate, zinc acetate or magnesium acetate; Lewis acids such as ferric chloride, zinc chloride, potassium dihydrogen phosphate, sodium dihydrogen phosphate, calcium dihydrogen phosphate, ammonium dihydrogen phosphate, potassium dihydrogen pyrophosphate, sodium dihydrogen pyrophosphate, calcium dihydrogen pyrophosphate or boron trifluoride ether complex; and metal isopropoxides such as aluminum triisopropoxide or tetraisopropoxytitanium. Aromatic sulfonic acids, organotin compounds, phosphorus-containing inorganic or organic acids and acidic phosphates or pyrophosphates are preferable. Particularly preferred are phosphorus based inorganic or organic acids and acidic phosphates or pyrophosphates. These catalysts are advantageous because they substantially prevent various side reactions from occurring and can be easily removed from the end product by absorption or filteration.

A number of polymerization inhibitors are known in the art. Examples of usable inhibitors include hydroquinone, p-methoxyphenol, 2,6-di-t-butyl-4-methylphenol (BHT), t-butylhydroxyanisole (BHA), 4-t-butylcatechol, bis(dihydroxybenzyl)benzene, 2,2'-methylenbis(6-t-butyl-3-methylphenol), 4,4-thiobis(6-t-butyl-3-methylphenol), N-nitrosophenylhydroxylamine ammonium salt, 1,1-diphenyl-2-picrylhydrazil, 1,3,5-triphenylpheldazil, dithiobenzoylsulfide, p,p'-ditolyltrisulfide, p,p'-ditolyltetrasulfide, dibenzyltetrasulfide, tetraethylthiuramsulfide, 2,2'-ethylidenebis(4,6-di-t-butylphenol), 2,2'-methylenebis(4-methyl-6-t-butylphenol) or tetrakis[methylene 3-(3,5-di-t-butyl-4-hydroxyphenyl) propionate].

An excess, generally from 2 to 30 times, preferably from 3 to 15 times molar excess of a dialkyl malonate relative to a hydroxyalkyl (meth)acrylate or polyoxyalkylene glycol mono(meth)acrylate is used in the reaction. The reaction is carried out by heating both reactants in the presence of a catalyst and a polymerization inhibitor to a temperature from 50 to 200° C., preferably from 70 to 150° C. while bubbling with a gas such as air or nitrogen or argon. As the reaction proceeds an alcohol corresponding to the alkyl group of the dialkyl malonate will be formed as a reaction by-product. This alcohol is removed from the reaction system. After the reaction, the remaining dialkyl malonate is distilled off from the reaction mixture in an evaporator or reaction vessel at a temperature from 70 to 140° C. under a vacuum from 0.01 to 30 Torr. If necessary, the product may be further purified by distillation at a temperature from 115 to 140° C. under a vacuum from 0.01 to 1.0 Torr. Recovered dialkyl malonate may be used repeatedly in the reaction as such or after purifying briefly.

Since the dialkyl malonate excessively added to the reaction system acts as a reaction solvent, it is normally not necessary to use a separate solvent. When necessary, however, an inert solvent such as hydrocarbons, ethers, ketones, esters, amides, nitriles or DMSO may be used.

The resulting malonate group-containing acrylate monomer of the above formul II may be copolymerized with other comonomers using a known method to produce an acrylic polymer which is capable of crosslinking with an α, β-unsaturated carbonyl compound or resin. Cured films produced from this acrylic polymer exhibit higher weatherability than the corresponding films produced from an acrylic polymer having acetoacetyl groups.

The following examples are intended to illustrate the invention without limiting thereto. All parts and percents therein are by weight unless otherwise specified.

EXAMPLE 1

A four necked flask equipped with a stirrer, a thermometer, an nitrogen gas tube, a Vigreaux column and a condenser was charged with a mixture of 130.14 g (1.0 mol) of 2-hydroxyethyl methacrylate (HEMA), 800.85 g (5.0 mol) of diethyl malonate, 4g (6.3 mmol) of dibutyltin dilaurate, and 8g (23 mmol) of 2,2'-methylenebis(4-methyl-6-t-butylphenol). The mixture was heated at 130° C. for 2 hours while vigorously bubbling with nitrogen gas. 40g (0.9 mol) of ethanol was recovered during the reaction period. Then the mixture was evaporated in an evaporator to remove excessive diethyl malonate, and purified by distillation under vacuum. 204g (83.5% of theory) of 2-(ethoxymalonyl-oxy)ethyl methacrylate was obtained as a liquid having b.p. of 133° C. /0.17 Torr.

$^1$H—NMR(CDCl$_3$): δ1.30(3H,t), 1.95 (3H, s), 3.40 (2H, s) , 4.21 (2H, t), 4.35 (2H, t), 4.41 (2H, t), 5.60 (1H, s), 6.13 (1H, s)

IR(neat): 2984, 1734, 1456, 1412, 1371, 1321, 1298, 1273, 1165, 1035, 949 cm$^{-1}$

EXAMPLE 2

The same flask as used in Example 1 was charged with a mixture of 130.14g (1.0 mol) of HEMA, 800.85g (5.0 mol) of diethyl malonate, 4g (23 mmol) of p-toluenesulfonic acid, and 8g (23 mmol) of 2,2'-methylenebis(4-methyl-6-t-butylphenol). The mixture was heated at 130° C. for 4 hours while vigorously bubbling with nitrogen gas. 38g (0.8 mol) of ethanol was recovered during the reaction period. Then the mixture was evaporated and purified as in Example 1 whereupon 213g (87.2% of theory) of 2-(ethoxymalonyloxy) ethyl methacrylate was obtained.

EXAMPLE 3

The same flask as used in Example 1 was charged with a mixture of 13.01 g (0.1 mol) of HEMA, 66.6g (0.5 mol) of dimethyl malonate, 0.4g (0.6 mmol) of dibutyltin dilaurate, and 0.8g (2.3 mmol) of 2,2'-methylenebis(4-methyl-6-t-phenol). The mixture was heated at 130° C. for 2 hours while vigorously bubbling with nitrogen gas. 2.5g (0.08 mol) of methanol was recovered during the reaction period. Then the mixture was evaporated and purified as in Example 1 to obtain 2-(methoxymalonyloxy)ethyl methacrylate.

EXAMPLE 4

The same flask as used in Example 1 was charged with a mixture of 6.51 g (0.05 mol) of HEMA, 160.17g (1.0 mol) of diethyl malonate, 0.2g (1 mmol) of dibutyltin dilaurate, and 0.4g (12 mmol) of 2,2'-methylenebis(4-methyl-6-t-butylphenol). The mixture was heated at 130° C. for 2 hours while vigorously bubbling with nitrogen gas. 2.0 g (0.04 mol) of ethanol was recovered during the reaction period. Then the mixture was evaporated and purified as in Example 1 to obtain 2-(ethoxymalonyloxy)ethyl methacrylate.

EXAMPLE 5

The same flask as used in Example 1 was charged with a mixture of 130.14g (1.0 mol) of HEMA, 800.85g (5.0 mol)

of diethyl malonate, 4g (21 mmol) of p-toluenesulfonic acid, and 8g (27 mmol) of 2,2'-methylenebis(4-methyl-6-t-butylphenol). The mixture was heated at 130 °C. for 4 hours while vigorously bubbling with nitrogen gas. 38g (0.8 mol) of ethanol was recovered during the reaction period. Then the mixture was evaporated and purified as in Example 1 to obtain 165g (67.4% of theory) of 2-(ethoxymalonyloxy) ethyl methacrylate.

EXAMPLE 6

The same flask as used in Example 1 was charged with a mixture of 130.14g (1.0 mol) of HEMA, 800.85g (5.0 mol) of diethyl malonate, 4g (6.3 mmol) of dibutyltin dilaurate, and 8g (36 mmol) of 2,2'-methylenebis(4-methyl-6-t-butylphenol). The mixture was heated at 70° C. for 8 hours while vigorously bubbling with nitrogen gas. 40g (0.8 mol) of ethanol was recovered during the reaction period. Then the mixture was evaporated and purified as in Example 1 to obtain 2-(ethoxymalonyloxy)ethyl methacrylate.

EXAMPLE 7

The same flask as used in Example 1 was charged with a mixture of 130.14g (1.0 mol) of HEMA, 940.96g (5.0 mol) of diisopropyl malonate, 4g (6.3 mmol) of dibutyltin dilaurate, and 8g (23 mmol) of 2,2'-methylenebis(4-methyl-6-t-butylphenol). The mixture was heated at 130° C. for 8 hours while vigorously bubbling with nitrogen gas. Then the mixture was evaporated and purified as in Example 1 to obtain 2-(isopropoxymalonyloxy)ethyl methacrylate.

EXAMPLE 8

The same flask as used in Example 1 was charged with a mixture of 13.01 g (0.1 mol) of HEMA, 108.11 g (0.5 mol) of di-t-butyl malonate, 0.4g (0.6 mmol) of dibutyltin dilaurate, and 0.8g (2.3 mmol) of 2,2'-methylenebis(4-methyl-6-t-butylphenol). The mixture was heated at 130° C. for 16 hours while vigorously bubbling with nitrogen gas. An amount of t-butanol was recovered during the reaction period. Then mixture was evaporated and purified as in Example 1 to obtain 2-(t-butoxymalonyloxy)ethyl methacrylate.

EXAMPLE 9

The same flask as used in Example 1 was charged with a mixture of 116.1 g (1.0 mol) of 2-hydroxyethyl acrylate (HEA) 800.85g (5.0 mol) of diethyl malonate, 4g (6.3 mmol) of dibutyltin dilaurate, and 8g (23 mmol) of 2,2'-methylenebis(4-methyl-6-t-butylphenol). The mixture was heated at 130° C. for 2 hours while vigorously bubbling with nitrogen gas. An amount of ethanol was recovered during the reaction period. Then mixture was evaporated and purified as in Example 1 to obtain 2-(ethoxymalonyloxy)ethyl acrylate.

EXAMPLE 10

The same flask as used in Example 1 was charged with a mixture of 1281.36g (8.0 mol) of diethyl malonate, 4.58g (34 mmol) of potassium dihydrogen phosphate, and 1.95 g (0.9 mmol) of 2,6-di-t-butyl-4-methylphenol. After raising the inner teperature to 130° C., 115.26g (0.8 mol) of 4-hydroxybutyl acrylate was added to the flask dropwise over 1 hour. After the addition, the mixture was heated at 130° C. for 4 hours while vigorously bubbling with nitrogen gas. 32.74g (0.7 mol) of ethanol was recovered during the reaction period. Then the mixture was filtered to remove potassium dihydrogen phosphate, and evaporated to remove remaining diethyl malonate. 196.18g (95% of theory) of 4-(ethoxymalonyloxy)butyl acrylate was obtained.

$^1$H—NMR(CDC$_3$): δ1.30(3H,t), 1.76 (4H, m), 3.38 (2H, s) , 4.20 (6H, m), 5.85 (1H, m), 6.11 (1H, m), 6.43 (1H, m)

IR(neat): 2962, 1732, 1410, 1332, 1271, 1192, 1153, 1035, 987, 812 cm$^{-1}$

EXAMPLE 11

The same flask as used in Example 1 was charged with a mixture of 13.01 g (0.1 mol) of HEMA, 108.11g (0.5 mol) of dibutyl malonate, 4g (6.3 mmol) of dibutyltin dilaurate, and 0.8g (2.3 mmol) of 2,2'-methylenebis(4-methyl-6-t-butylphenol). The mixture was heated at 130° C. for 12 hours while vigorously bubbling with nitrogen gas. An amount of butanol was recovered during the reaction period. Then the mixture was evaporated and purified as in Example 1 to obtain 2-(butoxymalonyloxy)ethyl methacrylate.

EXAMPLE 12

The same flask as used in Example 1 was charged with a mixture of 104.11g (0.8 mol) of HEMA, 1281.36g (8.0 mol) of diethyl malonate, 3.33g (34 mmol) of phosphoric acid, and 1.95g (0.9 mmol) of 2,6-di-t-butyl-4-methylphenol. The mixture was heated at 130° C. for 4 hours while vigorously bubbling with nitrogen gas. 34.35g (0.7 mol) of ethanol was recovered during the reaction period. Then the mixture was evaporated to remove remaining diethyl malonate. 193.44g (99.0% of theory) of 2-(ethoxymalonyloxy)ethyl methacrylate was obtained.

EXAMPLE 13

The same flask as used in Example 1 was charged with a mixture of 104.11 g (0.8 mol) of HEMA, 1281.36g (8.0 mol) of diethyl malonate, 6.05g (34 mmol) of pyrophosphoric acid, and 1.95g (0.9 mmol) of 2,6-di-t-butyl-4-methylphenol. The mixture was heated at 130° C. for 3 hours while vigorously bubbling with nitrogen gas. 33.95g (0.7 mol) of ethanol was recovered during the reaction period. Then the mixture was evaporated to remove remaining diethyl malonate. 192.40g (99.0% of theory) of 2-(ethoxymalonyloxy)ethyl methacrylate was obtained.

EXAMPLE 14

The same flask as used in Example 1 was charged with a mixture of 1281.36g (8.0 mol) of diethyl malonate, 4.58g (34 mmol) of potassium dihydrogen phosphates and 1.95g (0.9 mmol) of 2,6-di-t-butyl-4-methylphenol. After raising the inner temperature to 130° C., 104.11g (0.8 mol) of HEMA was added dropwise over 2 hours. Thereafter the mixture was heated at 130° C. while vigorously bubbling with nitrogen gas. 34.80g (0.7 mol) of ethanol was recovered during the reaction period. Then the mixture was filtered to remove potassium dihydrogen phosphate and evaporated to remove remaining diethyl malonate. 193.29g (99.0% of theory) of 2-(ethoxymalonyloxy)ethyl methacrylate was obtained.

EXAMPLE 15

The same flask as used in Example 1 was charged with a mixture of 104.11g (0.8 mol) of HEMA, 281.36g (8.0 mol) of diethyl malonate, 4.08g (34 mmol) of sodium dihydrogen phosphate, and 1.95g (0.9 mmol) of 2,6-di-t-butyl-4-methylphenol. The mixture was heated at 130° C. for 4 hours while vigorously bubbling with nitrogen gas. 34.97g (0.7 mol) of ethanol was recovered during the reaction period. Then the mixture was filtered to remove sodium dihydrogen phosphate and evaporated to remove remaining diethyl malonate. 193.14g (99.0% of theory) of 2-(ethoxymalonyl-oxy)ethyl methacrylate was obtained.

EXAMPLE 16

The same flask as used in Example 1 was charged with a mixture of 104.11 g (0.8 mol) of HEMA, 1281.36g (8.0 mol) of diethyl malonate, 7.96g (34 mmol) of sodium dihydrogen phosphate, and 1.95g (0.9 mmol) of 2,6-di-t-butyl-4-methylphenol. The mixture was heated at 130° C. for 4 hours while vigorously bubbling with nitrogen gas. 34.15g (0.7 mol) of ethanol was recovered during the reaction period. Then the mixture was filtered to remove sodium dihydrogen phosphate and evaporated to remove remaining diethyl malonate. 193.44g (99.0% of theory) of 2-(ethoxymalonyl-oxy)ethyl methacrylate was obtained.

EXAMPLE 17

The same flask as used in Example 1 was charged with a mixture of 1281.36g (8.0 mol) of diethyl malonate, 4.58g (34 mmol) of potassium dihydrogen phosphate, and 1.95g (0.9 mmol) of 2,6-di-t-butyl-4-methylphenol. After raising the inner teperature to 130° C., 174.48g (0.8 mol) of triethylene glycol monomethacrylate (MA-30 sold by Nippon Nyukazai Co., Ltd.) was added dropwise over 1 hour. After the addition, the mixture was heated at 130° C. for 4 hours. 32.21g (0.7 mol) of ethanol was recovered during the reactio period. Then the mixture was filtered to remove potassium dihydrogen phosphate and evaporated to remove remaiing diethyl malonate. 252.48g (95.0 % of theory) of triethylene glycol ethoxymalonate methacrylate was obtained.

$^1$H—NMR(CDCl$_3$): δ1.30(3h,t), 1.95 (3h, s), 3.41 (2H s), 3.66–3.70 (8h, m), 4.20–4.38 (6h, m) 5.58 (1h, m), 6.13 (1H, m)

IR(neat): 2957, 2876, 1734, 1637, 1456, 1371, 1321, 1298, 1166, 1037, 949 cm$^{-1}$

We claim:

1. A method for preparing a malonate group-containing acrylate monomer comprising:

heating a hydroxyl group-containing acrylic monomer of the formula:

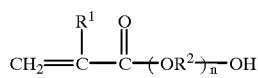

wherein R$^1$ is hydrogen or methyl, R$^2$ is a C$_2$–C$_6$-alkylene, and n is an integer from 1 to 10, and an excess of a dialkyl malonate in the presence of a catalyst and a polymerization inhibitor while bubbling with a gas; and removing an alcohol produced as a reaction by-product from the system during the heating step.

2. The method of claim 1, wherein said dialkyl malonate is a di-C$_1$–C$_{10}$-alkyl malonate.

3. The method of claim 1, wherein said catalyst is a Bronsted acid or base, a Lewis acid or base, or a solid acid or base.

4. The method of claim 1, wherein said catalyst is a phosphorus-containing inorganic or organic acid.

5. The method of claim 1, wherein said catalyst is an acidic phosphate or pyrophosphate salt.

6. The method of claim 1, wherein from 2 to 30 times excess in moles of said dialkyl malonate is used relative to said hydroxyl group-containing acrylic monomer.

7. The method of claim 1 further comprising removing excessive dialkyl malonate by evaporating or distillating the reaction product.

8. A method of claim 1, wherein said malonate group-containing acrylic monomer has the formula:

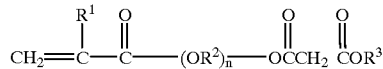

wherein R$^1$ is hydrogen or methyl, R$^2$ is a C$_2$–C$_6$-alkylene, R$^3$ is a C$_1$–C$_{10}$-alkyl, and n is an integer from 1 to 10 with the proviso that when R$^1$ is methyl, R$^2$ is ethylene and n is 1, R$^3$ cannot mean methyl wherein said malonate group-containing acrylic monomer is produced in a yield greater than 67.4% of theory.

9. A method of claim 8, wherein said acrylate monomer is 2-(ethoxymalonyloxy)ethyl methacrylate, 2-(isopropoxymalonyl-oxy)ethyl methacrylate, 2-(butoxymalonyloxy)ethyl methacrylate, 2-(ethoxymalonyloxy)ethyl acrylate, 4-(ethoxymalonyloxy) butyl acrylate or polyethylene glycol ethoxymnalonate methacrylate.

10. A method for preparing a malonate group-containing monomer of the formula.

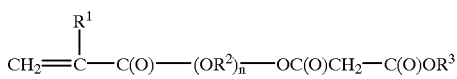

said method comprising:

heating a hyroxyl group-containing acrylic monomer of the formula:

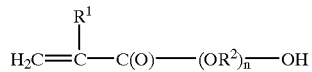

wherein R$^1$ is hydrogen or methyl, R$^2$ is a C$_2$ –C$_4$ alkylene, R$^3$ is a C$_1$–C$_{10}$ alkyl- and n is an integer from 1 to 10, and an excess of a dialkyl malonate in the presence of a catalyst and a polymerization inhibitor while bubbling with a gas; and removing alcohol produced as a reaction by-product from the system during the heating step wherein said malonate group-containing monomer is produced in a yield greater than 95% of theory.

* * * * *